United States Patent [19]
Veronesi et al.

[11] Patent Number: 5,464,870
[45] Date of Patent: Nov. 7, 1995

[54] METHODS OF INHIBITING DEVELOPMENT OF LEUKOPLAKIA WITH FENRETINIDE

[75] Inventors: Umberto Veronesi; Fausto Chiesa; Alberto Costa, all of Milan, Italy

[73] Assignee: Ortho Pharmaceutical Corporation, Raritan, N.J.

[21] Appl. No.: 15,944

[22] Filed: Feb. 10, 1993

[51] Int. Cl.$^6$ .................................................. A61K 31/165
[52] U.S. Cl. ................................................................ 514/617
[58] Field of Search .................................... 514/725, 617, 514/630

[56] References Cited

PUBLICATIONS

Chemical Abstracts 115: 41529r (1991).

*Primary Examiner*—Jerome D. Goldberg
*Attorney, Agent, or Firm*—Joseph J. Brindisi; Kenneth J. Dow

[57] ABSTRACT

This invention relates to methods of inhibiting development of leukoplakia or malignant lesions in a patient comprising the step of administering an effective leukoplakia or malignant lesion inhibiting amount of fenretinide to a patient wherein the administration of the fenretinide incurs less significant undesirable side effects than administration of other vitamin A retinoid derivatives.

10 Claims, No Drawings

METHODS OF INHIBITING DEVELOPMENT OF LEUKOPLAKIA WITH FENRETINIDE

FIELD OF THE INVENTION

This invention relates to methods of inhibiting development of leukoplakia or malignant lesions in a patient comprising the step of administering an effective leukoplakia inhibiting, or malignant lesion inhibiting amount of fenretinide to a patient wherein the administration of fenretinide incurs less significant undesirable side effects than administration of other vitamin A retinoid derivatives.

In more particular applications of the methods of the invention, fenretinide is post-operatively administered to oral leukoplakia patients wherein the fenretinide provides a chemo-preventative therapy for inhibiting local relapses or new localizations of leukoplakia or development of squamous cell carcinoma.

BACKGROUND OF THE INVENTION

Oral leukoplakia is a mucosal disease with a high canceration rate—estimated to range between 0% and 20% over 20 years, see e.g. Metha F. S., Pindborg J. J., Gupta P. C., Daftrary D. K. Epidemiologic and histologic study of oral cancer and leukoplakia among 50,915 villages in India, *Cancer* 1969, 24, 832–849. Surgical removal is considered the best therapy, see e.g. Frame J. W., Dasgupta A. R., Dalton G. A. Use of the carbon dioxide laser in the management of premalignant lesions of the oral mucosa, *J. Laryngol Otol* 1984, 98, 1251–1260. Many patients operated on for oral leukoplakia later develop local relapses, new leukoplakias or squamous cell carcinomas. This finding is consistent with the field cancerization concept introduced by Slaughter in 1953 for head and neck cancers: a whole tissue region repeatedly exposed to carcinogenic insult (tobacco, alcohol) is at an increased risk for developing multiple independent foci of malignant lesions see e.g., Slaughter D. P., Soutwick H. W., Smejkal W. *"Field cancerization"* in oral stratified squamous epithelium: clinical implications of multicentric origin, *Cancer* 1953, 6, 963–968. These considerations were believed by the inventors to justify chemopreventive trials and the accessibility to the oral cavity allows convenient histological, photographic and size evaluation to assess intervention efficacy.

Over the last 10 years several studies have indicated that vitamin A and its derivatives are effective in the treatment of oral leukoplakias, although the mechanisms of such action are not completely understood. See e.g., Koch H. F., Biochemical treatment of precancerous oral lesions: the effectiveness of various analogues of retinoic acid. *J. Maxillofac Surg.* 1978, 6, 59–63; Shah J. P., Strong E. W., Decosse J. J., Iri L., Sellers P. Effect of retinoids on oral leukoplakia, *Am. J. Surg.* 1983, 146, 466–470; Stich H. F., Hornby A. P., Dunn B. P. A pilot beta-carotene interventional trial within units using smokeless tobacco, *Int. J. Cancer* 1985, 36, 321–327; Hong W. K., Endicott J., Itri L. M. et al. 13-cis-retinoic acid in the treatment of oral leukoplakia; *N. Engl. J. Med.* 1986, 315, 1501–1505; and Garewal H. S., Meyskens F. L. Jr., Killen D., et al. Response of oral leukoplakia to beta-carotene. *J. Clin. Oncol.* 1990, 8, 1715–1720. These compounds have also been shown to be effective in modulating the growth of premalignant cells and suppressing their progression to neoplasia, see e.g., Meyskens F. L. Chemoprevention, In: *Wittes* R. E., ed. Cancer Investigation and Management. Chichester, John Wiley & Sons, 1985, 2, 275–283. In a recent randomized study it was shown that 13-cis-retinoic acid is efficacious in preventing the development of second primary tumors in patients disease-free after local therapy for squamous cell carcinoma of the head and neck, Hong W. K., Lippman S. M., Itri L. M., et al. Prevention of second primary tumors with isotretinoin in squamous cell carcinoma of the head and neck. *N. Engl. F. Med.* 1990, 323, 795–801.

Despite the effectiveness of such retinoid treatments, it has been universally found that therapeutic doses of these retinoids cause severe side effects (skin dryness, cheilitis, hypertriglicer-dermia and conjunctivitis) and many patients are unable to continue therapy, Sporn MB, Newton DL. Chemoprevention of cancer with retinoids, Fed. Proc. 1979, 38, 2528–2534. It is therefore an object of the present invention to provide a retinoid which is therapeutically effective for treating leukoplakia and inhibiting the development of malignant lesions but is safely tolerated by patients being treated thereby.

SUMMARY OF THE INVENTION

As embodied and fully described herein, the present invention most broadly provides a method of inhibiting development of leukoplakia or malignant lesions in a patient comprising the step of administering an effective leukoplakia or malignant lesion inhibiting amount of fenretinide to a patient wherein the administration of fenretinide incurs less significant undesirable side effects then administration of other naturally occurring and synthetic vitamin A retinoid derivatives. In particular fenretinide may be used for treating post-operative oral leukoplakia patients to inhibit the development of a recurrence of leukoplakia, new leukoplakia or malignant lesions. In particular embodiments, an effective leukoplakia or malignant lesion inhibiting amount of fenretinide is administered to a post-operative oral leukoplakia patient wherein the administration of fenretinide incurs less significant undesirable side effects than administration of other vitamin A retinoid derivatives.

In other embodiments of the invention a chemopreventative adjacent therapy is provided for inhibiting local relapses or new localizations of leukoplakia or the development of squamous cell carcinomas comprising the steps of resection of oral leukoplakia in a patient and post-operatively administering fenretinide in an amount effective to inhibit local relapse or new localizations of leukoplakia or to inhibit the development of squamous cell carcinomas while incurring less significant undesirable side effects than administration of other natural or synthetic vitamin A retinoids.

In other preferred embodiments of the methods of the invention the fenretinide is administered on a daily basis but is interrupted for at least three days after from about day 21 to 28 of administration and the daily administration is continued following such interruption.

DETAILED DESCRIPTION OF THE PREFERRED EMBODIMENTS

Reference will now be made in detail to particularly preferred embodiments of the invention. An example of a method of treatment carried out in accordance with the preferred embodiments of the invention are illustrated in the following Examples section.

The present invention provides a method of using fenretinide for inhibiting the development of leukoplakia or malignant lesions while incurring less significant side effects than administration of other vitamin A retinoid derivatives.

Fenretinide or N-(4-hydroxyphenyl)-retinamide (4-HPR) is a synthetic retinoid having the formula:

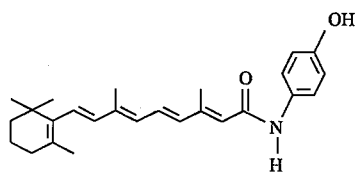

Fenretinide is a yellow, sweet smelling, tasteless solid which exhibits very low solubility in aqueous systems, most pharmaceutical solvents and most oils.

Fenretinide has proved to be safer and less teratogenic than other retinoids and is effective in preventing tumors in various organs in rodents Costa A., Malone W., Perloff M., et al. Tolerability of the synthetic retinoid fenretinide (4-HPR), *Eur. J. Cancer Clin. Oncol.* 1989, 25, 805–808. Unlike naturally occurring retinoids such as retinyl acetate or retinoic acid, which are stored in-the liver and can cause hepatototixicity, fenretinide does not accumulate in the liver and thus, may avoid the dose-limiting hepatotoxicity which is characteristic of retinoid toxicity.

As embodied and fully described herein, the present invention most broadly provides a method of inhibiting development of leukoplakia or malignant lesions in a patient comprising the step of administering an effective leukoplakia or malignant lesion inhibiting amount of fenretinide to a patient wherein the administration of fenretinide incurs less significant undesirable side effects than administration of other naturally occurring and synthetic vitamin A retinoid derivatives.

In particular, fenretinide may be used for treating post-operative oral leukoplakia patients to inhibit the development of recurring leukoplakia, new leukoplakia or malignant lesions. Fenretinide may also be applied as a chemopreventative adjuvant therapy for inhibiting local relapses or new localizations of leukoplakia or the development of squamous cell carcinomas. In accordance with this therapy resection of oral leukoplakia in a patient is followed by administration of fenretinide in an amount effective to inhibit local relapse or new localizations of leukoplakia or to inhibit the development of squamous cell carcinomas while incurring less significant undesirable side effects than by administration of other natural or synthetic vitamin A retinoids.

In accordance with particularly preferred methods of the invention the fenretinide is administered on a daily basis but is interrupted for at least three days after from about day 21 to 28 of administration and daily administration is continued following this at least three day interruption. Such a three day "drug holiday" regimen of treatment appears to avoid a potential side effect of reversible reduction of plasma retinoid levels and possible decrease or impairment of light vision.

It is especially advantageous to formulate the aforementioned fenretinide compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76–93, "Pharmaceutical Preparations and Their Manufacture", pp. 1409–1677 (1985). Particularly preferred however is a unit dosage form containing 100 mg. of fenretinide in a corn oil/polysorbate based formulation prepared in accordance with the disclosure of U.S. Pat. No. 4,655,098 to Gibbs et al., the entire disclosure of this patent is hereby incorporated herein by reference.

In therapeutic use fenretinide utilized in the methods of this invention may be administered to a patient either orally or parenterally at amounts effective to inhibit the development or reoccurrence of leukoplakia, malignant lesions, or squamous cell carcinomas. The effective dosages, however, may be varied depending upon the results of specific clinical testing, the requirements of the patient, the weight and age of the patient, the severity of the condition being treated, and the formulation being employed. Determination of optimum dosages for a particular situation is within the skill of the art. Effective dosage amounts may be in the range of from about 50–500 mg per day and preferably about 200 mg per day.

Certain other Vitamin A retinoids have been found effective by the prior art to treat leukoplakia but provide an unacceptable level of undesirable side effects such as severe skin dryness, cheilitis, hypertriglicerdermia and conjunctivitis. These other retinoids include, for example, 13-cis-retinoic acid, beta-carotene, isotretinoin and eletrinate. The present invention provides a marked increase in the therapeutic index of effectiveness/safety by providing comparable effectiveness but avoiding severe side effects by using less toxic fenretinide instead of such other Vitamin A retinoids.

The invention will now be illustrated by Examples. The Examples are not intended to be limiting of the scope of the present invention but read in conjunction with the detailed and general description above, provide further understanding of the invention and outline a method for carrying out the intended treatment of the invention.

EXAMPLES

The following ingredients and procedures for practicing the methods of the present invention correspond to that described above. The procedures below describe with particularity a presently preferred embodiment of the method of the invention for the post-operative treatment of oral leukoplakia to inhibit local relapses or new localization of leukoplakia or to inhibit the development of squamous cell carcinoma. Any methods, procedures, starting materials, reagents or excipients which are not particularly described will be generally known and available to those skilled in the medical and pharmaceutical arts.

The methods of the invention are demonstrated by a randomized chemo-prevention trials in patients specifically treated for oral leukoplakia. Eighty (80) patients who have had oral leukoplakia removed by surgical excision were divided into two groups, 41 in a control group and 39 in the group to receive 200 mg of fenretinide daily for 52 weeks. The procedures provided in this exempletive chemo-prevention trial are provided below:

Eighty (80) patients were diagnosed with oral leukoplakia lesions. Laser resections of the oral leukoplakia was performed under local anesthesia for all 80 patients. The wound was left open and the patients checked weekly to complete epithelialization.

39 of the 80 patients were administered 200 mg (i.e. 2 capsules) per day of fenretinide for a maximum of 52 weeks. Each patient received a three day holiday from the drug at the end of each month since it was discovered that fenretinide may cause a reversible reduction of plasma retinol levels if given continuously for more than one month.

The fenretinide was delivered in a soft gelatin capsule containing 100 mg. of fenretinide in a corn oil/polysorbate based formulation prepared in accordance with the disclosure of U.S. Pat. No. 4,655,098 to Gibbs et al., the entire disclosure of this patent is incorporated herein by reference.

Patients were checked every two months. The check-up includes clinical examination and metabolic, liver and renal function laboratory tests. When toxicity occurs, patients are checked at monthly intervals. All suspected lesions are photographed, biopsied and evaluated by a head and neck surgeon who does not know to which arm of the study the patient has been randomized. New lesions separated from the first-treated leukoplakias by more than 2 cm are considered new localizations. Time of appearance is calculated from the date of randomization. Patients with local relapses and new localizations are treated again by $CO_2$ laser exeresis. If squamous cell carcinoma develops, patients are treated according to established INT therapeutic procedure.

Control group patients are followed in the same way as those of the fenretinide group.

Patients completing the one-year study will be checked every 3 months during the subsequent year, every 4 months the year after and subsequently every 6 months. Also evaluated are plasma levels of retinol at baseline and of retinol, fenretinide and its metabolite N-(4-methoxyphenyl)-retinamide at 4 months, at the end of treatment and once a year during follow-up.

Toxicity is evaluated on the basis of subjective and objective symptoms and by assessment of blood parameters: bilirubin, cholesterol, triglycerides, Gama GT, GOT, and GPT. Mild toxicity is defined as increased by laboratory values 2–3 times above the upper normal limit. Severe toxicity is defined as values more than 3 times the upper normal limit. Evaluation of the severity of signs and symptoms is left to the clinician. Dermatitis, photodermatosis or impaired night vision with positive electroretinography are considered to be symptoms of toxicity. Results of a study of local relapses and new localizations of leukoplakia in patients in the study group are provided below in Table 1.

TABLE 1

| | (Occurrences/Patients) | |
| --- | --- | --- |
| | Control | Fenretinide |
| Local relapses | 5/41 | 2/39 |
| New localizations | 7/41 | 1/39 |
| Total | 12/41 | 3/39 |

Results

Patients were seen every 2 months in the absence of side effects and every month when complaints were observed, thus detailed information on toxicity and failure was available. It should further be reported that 2 patient deaths occurred in the control group and none occurred in the fenretinide treated group during the study. The results shown in Table 1 reveal a trend in the rate of effectiveness of fenretinide treatment in accordance with the invention which is comparable to treatment with other vitamin A retinoids.

Fenretinide was found to be less toxic than other synthetic retinoids and is well-tolerated by patients. The present study thus confirming findings of the following studies: Costa A., Malone W., Perloff M. et al. Tolerability of the synthetic retinoid fenretinide (4-HPR) *Eur. J. Cancer Clin. Oncol.* 1989, 25, 805–808; Rotsmensz N., DePalo G., Formelli F., et al. Long term tolerability of fenretinide (4-HPR) in breast cancer patients, *Eur. J. Cancer* 1991, 2, 1127–1131; and Formelli F., Carsana R., Costa A., et al. Plasma retinol level reduction by the synthetic retinoid fenretinide: a one year follow-up study of breast cancer patients, *Cancer Res.* 1989, 49, 6149–6152. Two patients (1 in the fenretinide group and 1 in the control group) suffered myocardial infarction during the treatment period. A total of 18/32 (54.3%) patients had some complaint during this time but only 5/32 (15.6%) did not complete the intervention because of toxicity. These findings are lower than those observed by other authors using synthetic retinoids (isotretinoin or etetrinate). Statistical evaluation of toxicity shows no difference in blood parameters between the two groups. Although 3 patients in the fenretinide group developed high blood triglyceride levels during the period, they returned similar values when rechecked 1 month after suspending fenretinide. It is concluded from this study that fenretinide is relatively well-tolerated and that dermatitis is the only side effect to be expected.

Due to fenretinide's promising trend of effectiveness for inhibiting local relapses and especially new localizations of leukoplakias and its relatively low toxicity, its method of use in accordance with the invention is thus observed to have a higher therapeutic index of effectiveness/safety as compared to the use of other vitamin A retinoid derivatives for treating post-operative leukoplakia patients and other related chemopreventive therapies.

The scope of the present invention is not limited by description, examples and suggested methods described herein and modifications can be made without departing from the spirit of the invention. For example, other adjuvant surgical or chemo-preventative therapies may be used in combination with the method of the present invention. Further, additional medicaments or active components may be used in combination with the compounds of the invention.

Applications of the compositions, processes, and method of the present invention can be accomplished by any medical and pharmaceutical methods and techniques as are presently or prospectively known to those skilled in the art. It is intended that the invention cover any modifications and variations of this invention provided that they come within the scope of the appended claims and their equivalents.

What is claimed is:

1. A method of inhibiting development of leukoplakia in a patient diagnosed with leukoplakia comprising the step of administering an effective leukoplakia inhibiting amount of fenretinide to the patient.

2. The method according to claim 1 wherein the fenretinide is administered in accordance with the regimen of administering fenretinide on a daily basis but interrupting the administration for at least three days after from 21 to 28 days of administration and continuing the daily administration following said at least three day interruption.

3. The method of claim 1 wherein the fenretinide is administered to a patient at an effective daily dosage level of from about 50 to 500 mg.

4. The method of claim 2 wherein the effective daily dosing of fenretinide is about 200 mg.

5. A method of treating post-operative oral leukoplakia patients to inhibit the development of a recurrence of leukoplakia or new leukoplakia comprising the step of administering an effective leukplakia inhibiting amount of fenretinide to the post-operative oral leukoplakia patient.

6. The method according to claim 5 wherein the fenretinide is administered in accordance with the regimen of administering fenretinide on a daily basis but interrupting the administration for at least three days after from 21 to 28 days of administration and continuing the daily administration following said at least three day interruption.

7. The method of claim 5 wherein the fenretinide is administered to a patient at an effective daily dosage level of from about 50 to 500 mg.

8. The method of claim 5 wherein the effective daily dosing of fenretinide is about 200 mg.

9. The method of claim 8 wherein the fenretinide is administered to a patient at an effective daily dosage level of from about 50 to 500 mg.

10. The method of claim 8 wherein the effective daily dosing of fenretinide is about 200 mg.

* * * * *